United States Patent [19]

Sand et al.

[11] Patent Number: 5,118,428

[45] Date of Patent: Jun. 2, 1992

[54] METHOD TO REMOVE RED BLOOD CELLS FROM WHOLE BLOOD SAMPLES

[75] Inventors: Theodore T. Sand, Poway; Barbara McLaughlin, Ramona; William P. Kolb, Del Mar, all of Calif.

[73] Assignee: Quidel, San Diego, Calif.

[21] Appl. No.: 612,394

[22] Filed: Nov. 13, 1990

[51] Int. Cl.⁵ .............................................. B01D 24/02
[52] U.S. Cl. ...................... 210/749; 210/767; 210/782; 210/198.1; 210/491; 210/496; 210/505; 422/56; 422/61; 422/101; 436/63; 436/169; 436/177
[58] Field of Search .............. 210/651, 702, 749, 767, 210/198.1, 489, 491, 496, 503, 505, 729, 782; 422/56, 61, 73, 101; 436/63, 169, 177, 178

[56] References Cited

U.S. PATENT DOCUMENTS

| | | | |
|---|---|---|---|
| 3,552,928 | 1/1971 | Fetter | 422/56 |
| 3,657,116 | 4/1972 | Haller | 210/656 |
| 3,883,304 | 5/1975 | Hamilton | 436/65 |
| 4,358,288 | 11/1982 | Goldman | 422/61 |
| 4,477,575 | 10/1984 | Vogel et al. | 210/767 |
| 4,678,757 | 7/1987 | Rapkin et al. | 436/177 |
| 4,786,603 | 11/1988 | Weilinger | 210/509 |

FOREIGN PATENT DOCUMENTS 0287731 10/1988 European Pat. Off. .
0325413 7/1989 European Pat. Off. .

*Primary Examiner*—W. Gary Jones
*Attorney, Agent, or Firm*—Morrison & Foerster

[57] ABSTRACT

Red Blood Cells (RBC's) are removed from whole blood samples by contacting the whole blood sample with a solution containing an acid selected from the group consisting of acetic acid, citric acid, ascorbic acid, lactic acid, maleic acid, malic acid, and malonic acid. The agglutinated RBC's are then removed from the resultant suspension by procedures of filtration, centrifugation or decantation, leaving an essentially RBC-free serum or plasma sample.

10 Claims, No Drawings

METHOD TO REMOVE RED BLOOD CELLS FROM WHOLE BLOOD SAMPLES

TECHNICAL FIELD

The present invention relates to a process for the removal of red blood cells (RBC's) from whole blood lo samples. In one embodiment, it relates to contacting a whole blood sample with a solution containing an acid selected from the group consisting of acetic acid, citric acid, ascorbic acid, lactic acid, maleic acid, malic acid, and malonic acid. The agglutinated RBC's are removed from the resultant suspension and the remaining serum or plasma sample is available for chromogenic analysis of dissolved blood components.

BACKGROUND OF THE INVENTION

Blood fractionation is important in clinical chemistry. Chromogenic analysis is used to determine the concentration of particular components dissolved in the blood. The presence of a particular component is signaled by color production or color change. The presence of erythrocytes (RBC's) in the whole blood disturbs the reading of the chromogenic analysis due to the turbidity and color of the whole blood. It is therefore an object of the present invention to develop a simple and cost effective method for removal of the RBC's in the whole blood prior to the use of the remaining serum or plasma in the analysis of dissolved blood components.

Previous investigators have described methods for separating plasma or serum from whole blood. EPO Publication No. 325413 to Jeong et al. describes a method and device for separating plasma from RBC's which involves contacting a polycationic surface with whole blood and having the RBC's bind to the surface leaving the plasma free of RBC's. Steric chromatography is used to separate plasma or serum components from whole blood in U.S. Pat. No. 3,657,116 to Haller. The plasma or serum is prefractionated using a precipitant. The precipitant-containing plasma or serum fraction is introduced into a porous-glass filled chromatographic column and the plasma or serum is thereby separated from the precipitant. U.S. Pat. No. 4,786,603 to Weilinger et al. describes coagulation-neutral hydrophilic glass fibers which can be used for the separation of plasma from whole blood. Additionally, U.S. Pat. No. 4,477,575 to Vogel et al. describes a composition and process for separating plasma or serum from whole blood wherein the whole blood is passed through a layer of glass fibers and the plasma or serum that is separated from the whole blood becomes available at the other side of the layer.

Other workers have described devices which both separate out the RBC'S from a whole blood sample and analyze the resultant plasma or serum for a particular dissolved component. EPO Publication No. 287731 to Maddox describes a dry test device comprising an absorbent reagent zone containing a chemical assay or immunoassay and an analyte target having a polysaccharide material that can limit the passage of RBC's or hold the RBC's on or near the surface of the absorbent reagent zone. A one-step procedure, employing simultaneous separation of fluid from whole blood with testing for a desired component is described in U.S. Pat. No. 4,678,757 to Rapkin et al. Blood is applied to the surface of a carbohydrate-treated carrier. The fluid portion migrates away from the point of contact and the cellular components remain in close proximity to the point of contact. If the carrier is further treated with a reagent employed to detect a component, a color will appear in the fluid. U.S. Pat. No. 3,552,928 to Fetter describes a means for separation of whole blood into a colorless fluid and a red cell or residue component. The whole blood is contacted with a separative reagent (a water-soluble, non-volatile amino acid), the residue is removed and the remaining fluid can be contacted with a test reagent. Both reagents may be contained on a single matrix (i.e. bibulous filter paper), however, the matrix must allow the colorless fluid to flow from the separating reagent to the test reagent.

DISCLOSURE OF THE INVENTION

Chromogenic and chromophoric analysis of particular components dissolved in blood is important for diagnostic purposes. Red blood cells (RBC's) hinder this type of analysis because they cause the sample to be colored and turbid, thereby obscuring any color change that would occur during chromogenic analysis. The invention, therefore, allows for the removal of the RBC's from a whole blood sample. Although the prior art describes removal of RBC's from whole blood, the one or two-step economical and efficient approach of the present invention is not suggested in the prior art.

One aspect of the invention is a process for separating plasma or serum from whole blood. The process comprises contacting whole blood with a solution containing an acid selected from the group consisting of acetic acid, citric acid, ascorbic acid, lactic acid, maleic acid, malic acid and malonic acid in a concentration, in an amount, at a pH, and for a period sufficient to agglutinate the RBC's in the blood. The process further comprises removing the RBC's from the resultant suspension by procedures based on filtration, centrifugation or decantation and obtaining essentially RBC-free serum or plasma that can be used for chromogenic/chromophoric analysis of dissolved blood components. In one embodiment, the RBC's can be removed in a single step wherein the acid is added to the blood in a tube to which an effective filter is attached, or in a matrix where separation is integral.

Another aspect of the invention is directed to a test device for detecting dissolved blood components in serum or plasma samples. The device comprises a first matrix containing an acid solution, the acid selected from the group consisting of acetic acid, citric acid, ascorbic acid, lactic acid, maleic acid, malic acid, and malonic acid, and a second matrix containing a test reagent. The acid solution in the first matrix acts to agglutinate the RBC's in a whole blood sample and the serum or plasma then passes to the second matrix wherein the test reagent allows for chromogenic/-chromophoric analysis of dissolved blood components.

Yet another aspect of the invention is directed toward a kit for carrying out the above process for separating plasma or serum from whole blood. The kit comprises a package containing a specified amount of an acid solution, the acid being selected from the group consisting of acetic acid, citric acid, ascorbic acid, lactic acid, maleic acid, malic acid, and malonic acid, which when added to a specified amount of whole blood will agglutinate the RBC's present in the whole blood. The kit further comprises a fibrous filter that can be used to remove the agglutinated RBC's from the suspension, leaving a serum or plasma sample for use in the analysis of dissolved blood components.

MODES FOR CARRYING OUT THE INVENTION

The invention is useful for the removal of RBC's from whole blood which is necessary in order to analyze particular dissolved blood components for diagnostic purposes In typical tests, the whole blood sample volume is between 10 µl and 50 ml, is preferably 10 µl to 1 ml and is more preferably 10 µl to 100 µl. To the blood sample is added an acid solution in a ratio by volume of approximately 1 part whole blood to 1-10 parts acid solution, and preferably 1 part whole blood to 5 parts acid solution. The acid solution is a 0.01 to 5.0 M acid solution, is preferably a 0.05 to 1.0M acid solution and has a pH effective to mediate the agglutination of the RBCs. In the case of most of the acids useful in the invention, the pH is such that at least one carboxyl group is in the salt form (except for acetic and citric acids which are in the free acid form).

The acid solution and whole blood mixture is contacted for a period of time, usually approximately 30 seconds or less, sufficient to allow for the near complete agglutination of the RBC's. The RBC's are removed from the suspension by procedures involving filtration, centrifugation, or decantation. In a preferred embodiment, the suspension is passed through a fibrous filter made of glass wool, cotton, glass fiber, or a combination of the materials. Preferably the filter is a combination of glass fiber and cotton, and most preferably the filter is a dispensetube tip with glass fiber (Whatman AP25) and cotton. Following filtration, the clear, essentially RBC-free plasma or serum sample is available for chromogenic analysis of the dissolved blood components.

The test system of the present invention may comprise a dual matrix system, each matrix being in fluid communication with the other matrix. The whole blood sample must initially contact the first matrix containing the acid solution in a concentration, in an amount, and at a pH sufficient to agglutinate the RBC's in the whole blood sample. The first matrix of the dual matrix system shall act as a fibrous filter such that the agglutinated RBC's remain on the first matrix and the RBC-free fluid shall flow to the second matrix containing the test reagent. The material of the dual matrix system may be cellulose fiber, the first matrix being impregnated with the acid solution, and the second matrix being impregnated with the appropriate test reagent.

The following example is intended to illustrate but not limit the invention.

EXAMPLE

Approximately 60 µl of whole blood was mixed in a tube with 300 µl of an acid solution (the solution comprising an acid listed below in a 0.85% sodium chloride solution). The mixture was incubated for 30 seconds. A tip (containing glass fiber and cotton) was attached, and the filtrate was dispensed into a test device.

The following table lists the acid solutions tested. The desired result was a clear filtrate and a strong signal.

|  | Form* | Concentration (M) | pH | Assay Signal | Filtrate |
| --- | --- | --- | --- | --- | --- |
| Acid |  |  |  |  |  |
| Acetic | FA | 1.0 | 1.9 | Weak | Clear |
| Acetic | FA | 0.2 | 2.6 | Strong | Clear |
| Citric | FA | 0.2 | 1.7 | Medium | Clear |
| Citric | FA | 0.05 | 2.1 | Medium | Clear |
| Ascorbic | S | 1.0 | 7.2 | Medium | Clear |
| Ascorbic | S | 0.5 | 7.2 | Medium | Clear |
| Ascorbic | FA | 1.0 | 1.9 | Weak | Clear |
| Ascorbic | FA | 0.25 | 2.4 | Medium | Clear |
| Lactic | FA | 1.0 | 1.9 | None | Chemical Reaction |
| Lactic | S | 1.0 | 5.9 | Medium | Clear |
| Lactic (methyl ester) | N/A | 1.0 | 3.1 | Weak | Slight Discoloration |
| Maleic | FA | 1.0 | 3.1 | None | Chemical Reaction |
| Maleic | S | 1.0 | 8.9 | Strong | Clear |
| Malic | FA | 1.0 | 1.8 | None | Chemical Reaction |
| Malic | S | 1.0 | 8.1 | Strong | Clear |
| Malonic | FA | 1.0 | 1.3 | None | Chemical Reaction |
| Malonic | S | 1.0 | 8.4 | Strong | Clear |
| Other Chemicals |  |  |  |  |  |
| Phenol | FA/S | 0.1 | 5.2 | None | No Flow |
| Ethyl Acetate | N/A | 1.0 | 5.4 | Very Weak | Heavy Discoloration |
| Tannic Acid | U | 1% sol. | 3.4 | None | Heavy Discoloration |

*FA — Free acid. S — Salt. N/A — Not Applicable. U — Unknown

The above results indicate that acetic acid, citric acid, ascorbic acid, lactic acid, maleic acid, malic acid, and malonic acid are appropriate acids to use for agglutination of the RBC's in the samples tested. They all produce clear solutions and give strong or at least medium signals when tested for color intensity in a serological assay.

I claim:

1. A process for removing Red Blood Cells (RBC's) from whole blood comprising:
   a) contacting a solution containing an acid from the group consisting of acetic acid, citric acid, ascorbic acid, lactic acid, maleic acid, malic acid and malonic acid, with a whole blood sample, the acid being present in a concentration and in an amount and at a pH effective to agglutinate the RBC's in the whole blood and obtain a resultant suspension; and
   b) removing the agglutinated RBC's from the resultant suspension by filtering the suspension through a fibrous material to produce an essentially RBC-free sample.

2. The process of claim 1 wherein the fibrous material is selected from the group consisting of glass wool, cotton, glass fiber or a combination thereof.

3. The process of claim 1 wherein the acid is acetic acid and the pH is of a value that maintains the acetic acid in predominantly the free acid form.

4. The process of claim 1 wherein the acid is citric acid and the pH is of a value that maintains the citric acid in predominantly the free acid form.

5. The process of claim 1 wherein the acid is ascorbic acid and the pH is of a value that maintains the ascorbic acid in predominantly the salt form.

6. The process of claim 1 wherein the acid is lactic acid and the pH is of a value that maintains the lactic acid in predominantly the salt form.

7. The process of claim 1 wherein the acid is maleic acid and the pH is of a value that maintains the maleic acid in predominantly the salt form.

8. The process of claim 1 wherein the acid is malic acid and the pH is of a value that maintains the malic acid in predominantly the salt form.

9. The process of claim 1 wherein the acid is malonic acid and the pH is of a value that maintains the malonic acid in predominantly the salt form.

10. A process for removing RBC's from whole blood comprising:
   a) contacting a solution containing an acid selected from the group consisting of acetic acid, citric acid, ascorbic acid, lactic acid, maleic acid, malic acid and malonic acid, with a whole blood sample, the acid being present in a concentration and in an amount and at a pH effective to agglutinate the RBC's in the whole blood and obtain a resultant suspension; and
   b) removing the agglutinated RBC's from the resultant suspension to produce an essentially RBC-free sample;
   wherein the removing is by filtering and wherein the filtering is carried out in a dispensetube tip containing glass fiber and cotton that dispenses the RBC-free sample onto a test device.

* * * * *